United States Patent [19]

Niwa et al.

[11] Patent Number: 5,087,455
[45] Date of Patent: Feb. 11, 1992

[54] HOLLOW GRANULAR MEDICINE AND ITS PREPARATION

[75] Inventors: Toshiyuki Niwa; Yoshiaki Kawashima; Hirofumi Takeuchi, all of Gifu; Yoji Ito, Toki, all of Japan

[73] Assignees: Showa Yakuhin Kako Co. Ltd.; Yoshiaki Kawashima, Japan

[21] Appl. No.: 585,670

[22] Filed: Sep. 20, 1990

Related U.S. Application Data

[62] Division of Ser. No. 367,948, Jun. 19, 1989.

[30] Foreign Application Priority Data

Oct. 18, 1988 [JP] Japan .................. 63-262550

[51] Int. Cl.$^5$ .............................................. A61K 9/16
[52] U.S. Cl. ...................... 424/497; 424/408; 424/451; 424/468; 424/470; 424/484; 424/489
[58] Field of Search .............. 424/451, 497, 470, 408, 424/468, 470, 489, 490, 484

[56] References Cited

U.S. PATENT DOCUMENTS

| | | | |
|---|---|---|---|
| 3,536,074 | 10/1970 | Aufhauser | 424/451 |
| 3,909,444 | 9/1975 | Anderson et al. | 428/402.24 |
| 4,150,110 | 4/1979 | Yoshida et al. | 424/491 |
| 4,205,060 | 5/1980 | Monsimer et al. | 424/495 |
| 4,411,754 | 10/1983 | Kaetsu et al. | 424/78 |
| 4,572,833 | 2/1986 | Pedersen | 424/470 |
| 4,606,909 | 8/1986 | Bechgaand et al. | 424/469 |
| 4,608,278 | 8/1986 | Frank et al. | 427/213.35 |
| 4,726,966 | 2/1988 | Kawashima et al. | 427/213.36 |
| 4,834,985 | 5/1989 | Elger | 424/484 |
| 4,844,905 | 7/1989 | Ichikawa | 424/451 |

OTHER PUBLICATIONS

Yasuo Nozawa and Fukuji Higashide, *Kobunshi Ronbunshu*, Nov. 1977, vol. 34, No. 11, 757-762, "Hole Formation in the Membrane of Polystyrene Microcapsules".

*Primary Examiner*—Thurman K. Page
*Assistant Examiner*—William E. Benston, Jr.
*Attorney, Agent, or Firm*—Oliff & Berridge

[57] ABSTRACT

A granular medicine with slow drug-release characteristics that is sufficiently absorbed in the intestines, in which the granular medicine has a hollow spherical structure, a drug is dispersed in the shell, which mainly consists of an enteron-soluble polymer. The method for preparing the medicine includes the steps of: (a) mixing a hydrophilic or hydrophobic drug with an enteron-soluble polymer in a mixture of an aliphatic alcohol and a chlorohydrocarbon; and (b) pouring this mixture into water or an aqueous medium, and stirring the solution to precipitate the medicine.

39 Claims, No Drawings

HOLLOW GRANULAR MEDICINE AND ITS PREPARATION

This is a division of application Ser. No. 07/367,948, filed June 19, 1989.

BACKGROUND OF THE INVENTION

This invention relates to a hollow granular medicine and its preparation, and more particularly, but not exclusively, to a granular medicine having a spherical structure and slow drug-release characteristics.

Oral drugs, which are promptly absorbed in the alimentary canal and are also rapidly lost from the blood, are generally film-coated or microcapsulated to cause the slow drug-release. These techniques, however, only delay the drug release and hence have a problem: while a drug can only be absorbed in the upper portion of small intestines, the drug might be released from a capsule or a pill after passing the absorption site. Even if slow drug release is attained, the drug that is released after passing the absorption site is not utilized, thus lowering the efficacy of the drug.

A drug whose solubility varies with pH generally differs between individuals in the incidence and duration of the effect. When the drug is treated to cause the slow drug release, it differs even more. Examples of such drugs include ibuprofen, ketoprofen and tranilast.

SUMMARY OF THE INVENTION

The objective of the invention is to provide a medicine with slow drug-release characteristics that produces fewer differences between individuals in effect and that has high utilization-efficiency, and also to provide a simple method of preparation of the drug.

The above and other related objectives are realized by a hollow granular medicine with a spherical structure, in which a drug is distributed in the shell mainly consisting of an enteron-soluble polymer.

A method for preparing this hollow granular medicine with a spherical structure, includes the steps of: (a) mixing a drug with an enteron-soluble polymer in a mixture of an aliphatic alcohol and a chlorohydrocarbon; and (b) pouring the resulting mixture into water or an aqueous medium, and stirring the solution to precipitate the medicine.

DESCRIPTION OF PREFERRED EMBODIMENT

A hydrophilic drug may be used in this invention but a hydrophobic one is generally preferable. Examples of such drugs include ibuprofen, ketoprofen, tranilast, 5-fluorouracil, tolbutamide, and indometacin.

A granular medicine of this invention has a spherical structure in which a drug is homogeneously distributed only in the shell, which mainly consists of an enteron-soluble polymer. The medicine has a coating of an enteron-soluble polymer that is insoluble in saliva and hence does not stimulate the tip of a tongue during administration. Since the medicine is hollow and its specific gravity is small, it floats in the stomach for a long while before being transported to an absorption site; so, the medicine possesses slow drug release characteristics. After being transported to the intestines, the medicine rapidly releases the drug component with the rise in pH, thus permitting the efficient absorption of the drug component.

The diameter of the granular medicine of the invention is 10 to 2,000 μm and thickness of the shell thereof is 1 to 200 μm.

The enteron-soluble polymer used may be an acrylic polymer or a cellulose polymer. The examples of the cellulose polymer include hydroxypropylmethylcellulose phthalate, hydroxypropylmethylcellulose acetate succinate, cellulose acetate phthalate, and carboxymethylethylcellulose. The acrylic polymer can be any enteron-soluble film-coating agent, for example, a copolymer of acrylate or methacrylate as shown in structural formulas I or II,

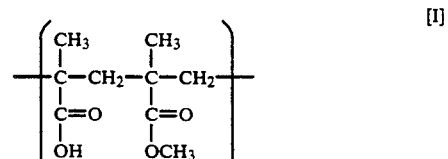

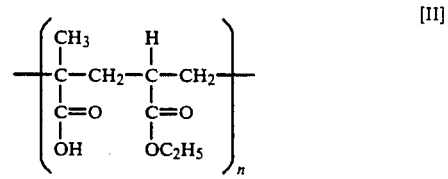

in which the molar ratio of acid to ester is preferably 1 to 1 to 1 to 2. This copolymer may be partially denaturated or copolymerized with a small amount of another monomer: for example, a quaternary ammonium group-containing copolymer as shown in formula III;

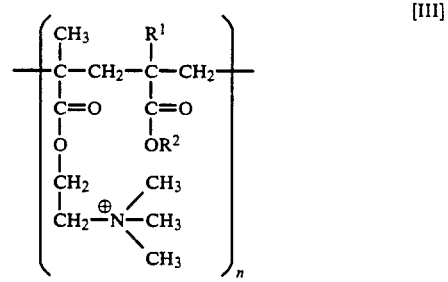

in which:
R¹ is —H, or —CH₃; and
R² is —CH₃, or —C₂H₅.

The molecular weight of the polymer used in this invention is generally 135,000 to 200,000.

To prepare this granular medicine, a powdery hydrophobic drug is mixed with an enteron-soluble polymer in a mixture of an aliphatic alcohol and a chlorohydrocarbon to prepare the mixed solution or suspension. The amount of the enteron-soluble polymer used may be 20 to 1,000 wt % with respect to the drug component, but 50 to 400 wt % is preferable. If the amount of the polymer is too large or too small, the object of the invention, hollow granular medicine, is not efficiently obtained.

The aliphatic alcohol used is a lower one containing one to four carbon atoms (e.g., methanol, ethanol, 2-propanol, and butanol). The chlorohydrocarbon used is an aliphatic one (e.g., methylene chloride, chloroform, ethylene chloride, and chloroethane). The amount of the chlorohydrocarbon used with respect to the aliphatic alcohol may be 0.5 to 2 times in volume, but 0.8 to 1.2 times in volume preferable. The total amount of both should be adjusted so that the drug concentration of the mixture becomes 0.1 to 20 wt %, preferably 0.5 to 10 wt %. The drug component may be mixed with the enteron-soluble polymer, the aliphatic alcohol, and the chlorohydrocarbon using any method. The mixing can be performed at room temperature. In this invention, the polymer solution above may include an organic solvent containing a hydroxyl group or a molten vehicle like wax to improve the plasticity of the polymer film and thus to obtain hollow granules with better shapes. The organic solvent may be, for example, propylene glycol, glycerine, or ethylene glycol. The vehicle may be, for example, monostearin, tristearin, stearic acid, cetyl alcohol, or stearyl alcohol. The amount of these agents used should be 1 to 100 wt % with respect to the enteron-soluble polymer.

The various homogeneously mixed components including the drug component, are then poured into water and are stirred, thus allowing the drug component to disperse and then allowing the hollow granules to precipitate. The amount of water used is 300 wt % or more, but 1,000 wt % or more is preferable. If the amount of water used is too small, cohesion of the particles of the components occurs during stirring, so high-quality hollow granules will not form.

This drug mixture may be mixed with water prior to stirring, or may be poured into the water while it is being stirred. The latter method is preferable because the drug component can homogeneously disperse and hollow granules with a better quality can be obtained. The stirring is carried out at a temperature of 20° to 60° C. for 5 through 300 minutes; preferably 30 through 150 minutes. The solution is stirred by a propeller-type agitator or a magnetic stirrer at 200 to 1,000 r.p.m.

Using a surfactant or a water-soluble polymer in the water is preferable since it improve granulation efficiency to produce better-quality hollow granular medicine. The surfactant may be anionic (e.g., sodium laurylsulfate, sodium benzenesulfonate, sodium laurylbenzensulfonate or sodium oleate), or it may be cationic (e.g., cetyltrimethylammonium bromide), or it may be nonionic (e.g., a polyoxyethylene sorbitan fatty acid ester, a monoester or triester of oleic acid, or a sorbitan fatty acid ester). The water-soluble polymer may be polyvinyl alcohol, polyethylene glycol, methylcellulose, or hydroxypropylcellulose.

The amount of the surfactant or the water-soluble polymer used is 1 to 300 wt % with respect to the drug component. If the amount used is too small, the effect of the additives is insufficient; but too large an amount is uneconomical since the effect levels off.

In this manner, a granular medicine with a spherical structure precipitates from the medium, in which the drug component is homogeneously dispersed in the shell, which mainly consists of an enteron-soluble polymer. The medicine has a film of the enteron-soluble polymer, and has a hollow that gives the medicine a low specific gravity. The size of granules deposited is normally 10 to 2,000 μm.

The hollow granules are then recovered from the mixture by solid-liquid separation, are washed with water, and are dried to remove the aliphatic alcohol and the chlorohydrocarbon used as the solvent. The granular medicine can be dried either chemically or physically (e.g., by warming, reducing pressure, or using a desiccant such as silica gel).

The drug component does not deteriorate in the process of the invention, thus maintaining its efficiency and safety unchanged.

Some examples of the invention are described now. Since there may be many modifications without departing from the scope of the invention, the examples below are not intended to limit the invention to the examples, but are intended to illustrate the invention more clearly.

EXAMPLE 1

1.5 g of powdery ibuprofen and 2.0 g of an enteron-soluble acrylic polymer are added to 10 ml of ethanol and 10 ml of dichloromethane in a 50 ml glass vessel, and are stirred by a magnetic stirrer for 60 minutes at room temperature so they are homogeneously mixed. The enteron-soluble acrylic polymer used is a copolymer of methacrylic acid and methyl methacrylate with a molecular weight of 135,000 (Röhn Pharma trademark "EUDRAGIT S" or "EUDRAGIT L").

While 200 ml of water including 0.025 wt % sodium laurylbenzenesulfonate is being stirred in a 500 ml glass vessel with a stirring wing at 300 r.p.m. at 40° C., the drug mixture is dropped into the water. The resulting solution is stirred for 60 minutes to deposit granules with the spherical hollow structure. The resulting deposit is filtered, washed with water, and then dried by the blowing air at 40° C. to recover the hollow granular ibuprofen of the present invention.

The size of the hollow granules obtained in our experiment was 630 μm on average and the yield was 90%. In oral administration, ibuprofen of the granular medicine does not stimulate the tip of a tongue, and does not prematurely deteriorate either. An elution test shows that the granuled ibuprofen of the sample has better drug release characteristics than original ibuprofen powders: the original drug ibuprofen, is released at a constant speed.

The medicine obtained has a spherical structure in which noncrystalline ibuprofen is distributed in the shell, which mainly consists of the enteron-soluble polymer The hollow granules of the sample float on water for four to five hours.

EXAMPLE 2

0.5 g of powdery tranilast and 1.0 g of an enteron-soluble acrylic polymer are added to 5 ml of ethanol and 5 ml of dichloromethane in a 50 ml glass vessel, and are stirred by a magnetic stirrer for 60 minutes at room temperature so they are homogeneously mixed. The enteron-soluble acrylic polymer used is a copolymer of methacrylic acid and methyl methacrylate with molecular weight of 135,000 (Röhm Pharma trademark "EUDRAGIT S").

While 200 ml of water including 0.5 wt % polyvinyl alcohol is being stirred in a 500 ml glass vessel with a stirring wing at 300 r.p.m. at 40° C., the drug mixture is dropped into the water. The resulting solution is stirred for 60 minutes to deposit granules with a spherical hollow structure. The resulting deposit is filtered, washed with water, and then dried by blowing air at 40° C. to recover the hollow granular tranilast of the present invention.

The size of the hollow granules obtained in our experiment was 410 μm on average and the yield was 80%. An elution test shows that the granuled tranilast of the sample has better drug release characteristics than original tranilast powders. The granuled tranilast does not deteriorate at all.

The medicine obtained has a spherical structure, in which tranilast is distributed in the shell, which mainly consists of the enteron-soluble polymer.

EXAMPLE 3

0.5 g of powdery 5-fluorouracil and 1.0 g of an enteron-soluble acrylic polymer are added to 5 ml of methanol, 5 ml of dichloromethane, and 0.01 g of propylene glycol in a 25 ml glass tube, and are shaked by a horizontal shaker for 60 minutes at room temperature so they are homogeneously mixed. The enteron-soluble acrylic polymer used is a copolymer of methacrylic acid and methyl methacrylate with molecular weight of 135,000 (Röhm Pharm trademarks "EUDRAGIT S" or "EUDRAGIT L").

While 200 ml of water including 0.5 wt % polyvinyl alcohol is being stirred in a 500 ml glass vessel with a stirring wing at 300 r.p.m. at 40° C., the drug mixture is dropped into the water. The resulting solution is stirred for 60 minutes to deposit granules with a spherical hollow structure. The resulting deposit is filtered, washed with water, and then vacuum dried for 24 hours to recover the hollow granular 5-fluorouracil of the present invention.

The size of the hollow granules obtained in our experiment was 500 μm on average and the yield was 75%. The granuled 5-fluorouracil does not deteriorate at all.

The medicine obtained has a spherical hollow structure, in which 5-fluorouracil is dispersed in the shell, which mainly consists of the enteron-soluble polymer.

We claim:

1. A method for preparing a hollow granular medicine with a spherical hollow structure, in which a drug is distributed in the shell of the structure that essentially consists of an enteric polymer, including the steps of:
    (a) mixing a drug with an enteric polymer in a mixture of an aliphatic alcohol and a chlorohydrocarbon, where the amount of the enteric polymer is from 20 to 1000% by weight with respect to the drug component;
    (b) pouring the resulting solution into an aqueous medium and stirring the solution to make the hollow granular medicine with the spherical hollow structure;
    (c) separating the hollow granular medicine from the solution;
    (d) rinsing the hollow granular medicine with water; and
    (e) drying the hollow granular medicine.

2. A method as claimed in claim 1, in which the drug is hydrophobic.

3. A method as claimed in claim 1, in which the aliphatic alcohol is a lower aliphatic alcohol containing one to four carbon atoms.

4. A method as claimed in claim 1, in which the chlorohydrocarbon is aliphatic.

5. A method as claimed in claim 1, in which a surfactant is added into the aqueous medium prior to stirring in step (b).

6. A method as claimed in claim 1, in which a water-soluble polymer is added into the aqueous medium in step (b).

7. A method as claimed in claim 1, in which an organic solvent having a hydroxyl group is added to the solution of the aliphatic alcohol and the chlorohydrocarbon in step (a).

8. A method as claimed in claim 1, in which an organic solvent including a wax molten vehicle is added to the solution of the aliphatic alcohol and the chlorohydrocarbon in step (a).

9. A method as claimed in claim 1, in which the drug is selected rom the group consisting of ibuprofen, ketoprofen, tranilast, 5-fluorouracil, tolbutamide, and indometacin.

10. A method as claimed in claim 1, in which the granular medicine is solid and the diameter of the medicine ranges from 10 to 2,000 μm and the thickness of the shell thereof is from 1 to 200 μm.

11. A method as claimed in claim 1, in which the enteric polymer is selected from the group consisting of an acrylic polymer and a cellulose polymer.

12. A method as claimed in claim 11, in which the cellulose polymer is selected from the group consisting of hydroxypropylmethylcellulose phthalate, hydroxyproplymethylcellulose acetate succinate, cellulose acetate phthalate, and carboxymethylethylcellulose.

13. A method as claimed in claim 11, in which the acrylic polymer is an enteric film-coating agent consisting of a copolymer of methacrylic ester.

14. A method as claimed in claim 13, in which the copolymer of methacrylic ester has a molar ratio of acid to ester of from 1:1 to 1:2.

15. A method as claimed in claim 11, in which the copolymer is partially denaturated or copolymerized with a small amount of another monomer of a quaternary ammonium group-containing copolymer.

16. A method as claimed in claim 11, in which the molecular weight of the polymer is from 135,000 to 200,000.

17. A method as claimed in claim 6, in which the amount of the water-soluble polymer is from 1 to 300% by weight with respect to the drug component.

18. A method as claimed in claim 1, in which the chlorohydrocarbon is selected from the group consisting of methylene chloride, chloroform, ethylene chloride, and chloroethane.

19. A method as claimed in claim 1, in which the amount of the chlorohydrocarbon with respect to the aliphatic alcohol is 0.5 to 2 times in volume.

20. A method as claimed in claim 1, in which the amount of the chlorohydrocarbon with respect to the aliphatic alcohol is 0.8 to 1.2 times in volume.

21. A method as claimed in claim 1, in which the total amount of the aliphatic alcohol and the chlorohydrocarbon is adjusted such that the drug concentration with respect to the resulting solution is 0.1 to 20% by weight.

22. A method as claimed in claim 8, in which the total amount of the aliphatic alcohol and the chlorohydrocarbon is adjusted such that the drug concentration with respect to the resulting solution is 0.5 to 10% by weight.

23. A method as claimed in claim 7, in which the organic solvent is selected from the group consisting of propylene glycol, glycerine, and ethylene glycol.

24. A method as claimed in claim 8, in which the molten vehicle is selected from the group consisting of monostrearin, tristearin, stearic acid, cetyl alcohol, and stearyl alcohol.

25. A method as claimed in claim 23, in which the amount of the organic solvent is from 1 to 100% by weight with respect to the enteric polymer.

26. A method as claimed in claim 24, in which the amount of the molten vehicle is from 1 to 100% by weight with respect to the enteric polymer.

27. A method as claimed in claim 1, in which the aqueous medium in step (b) is water, and the amount of water is 300% or more by weight with respect to the resulting solution.

28. A method as claimed in claim 27, in which the amount of water is 1000% or more by weight.

29. A method as claimed in claim 1, in which the resulting solution is mixed with the aqueous medium during stirring.

30. A method as claimed in claim 1, in which the solution is poured into the aqueous medium when the aqueous medium is being stirred to make the drug homogeneously disperse and form hollow granules.

31. A method as claimed in claim 1, in which the stirring is carried out at a temperature of between 20° and 60° C. for 5 to 300 minutes.

32. A method as claimed in claim 1, in which the resulting solution is stirred by a propeller agitator or a magnetic stirrer at 200 to 1,000 r.p.m.

33. A method as claimed in claim 5, in which the surfactant is an anionic surfactant.

34. A method as claimed in claim 5, in which the surfactant is a nonionic surfactant.

35. A method as claimed in claim 33, in which the surfactant is selected from the group consisting of sodium laurylsulfate, sodium benzenesulfonate, sodium laurylbenzenesulfonate, and sodium oleate.

36. A method as claimed in claim 34, in which the surfactant is selected from the group consisting of a polyoxyethylene sorbitan fatty acid ester, a monoester or triester of oleic acid, and a sorbitan fatty acid ester.

37. A method as claimed in claim 6, in which the water-soluble polymer is selected from the group consisting of polyvinyl alcohol, polyethylene glycol, methylcellulose, and hydroxyproplycellulose.

38. A method as claimed in claim 5, in which the amount of the surfactant is from 1 to 300% by weight with respect to the drug component.

39. A method as claimed in claim 1, wherein the amount of the enteric polymer is from 50 to 400% by weight with respect to the drug component.

* * * * *